United States Patent
Wu et al.

(10) Patent No.: US 11,116,450 B2
(45) Date of Patent: Sep. 14, 2021

(54) ELECTRODE ASSEMBLY HAVING SPINES WITH CONTROLLED FLEXIBILITY

(71) Applicant: Biosense Webster (Israel) Ltd., Yokneam (IL)

(72) Inventors: Steven Wu, San Jose, CA (US); Sungwoo Min, Fullerton, CA (US); Stuart Williams, Ontario, CA (US); Marisa Borja, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 674 days.

(21) Appl. No.: 15/454,775

(22) Filed: Mar. 9, 2017

(65) Prior Publication Data
US 2018/0256109 A1 Sep. 13, 2018

(51) Int. Cl.
*A61B 5/00* (2006.01)
*A61B 5/287* (2021.01)
*A61B 18/12* (2006.01)
*A61B 18/14* (2006.01)

(52) U.S. Cl.
CPC ............ *A61B 5/6858* (2013.01); *A61B 5/287* (2021.01); *A61B 5/686* (2013.01); *A61B 5/6852* (2013.01); *A61B 5/6859* (2013.01); *A61B 18/12* (2013.01); *A61B 18/1492* (2013.01); *A61B 2562/0209* (2013.01); *A61B 2562/125* (2013.01); *A61B 2562/222* (2013.01)

(58) Field of Classification Search
CPC ..... A61B 5/042; A61B 5/0422; A61B 5/6858; A61B 5/686; A61B 5/6859; A61B 17/07207; A61B 17/07292; A61B 2562/0209; A61B 2562/125; A61B 2562/222
See application file for complete search history.

(56) References Cited

U.S. PATENT DOCUMENTS

| | | | |
|---|---|---|---|
| 5,239,724 A | 8/1993 | Salecker et al. |
| 5,332,089 A | 7/1994 | Tillet et al. |
| 5,391,199 A | 2/1995 | Ben-Haim |
| 5,484,118 A | 1/1996 | Fujimura et al. |
| 5,618,612 A | 4/1997 | Gstrein |
| 5,690,963 A | 11/1997 | Spargo et al. |
| 5,772,590 A | 6/1998 | Webster, Jr. |
| 6,064,905 A | 5/2000 | Webster, Jr. et al. |
| 6,239,724 B1 | 5/2001 | Doron et al. |
| 6,332,089 B1 | 12/2001 | Acker et al. |

(Continued)

FOREIGN PATENT DOCUMENTS

WO 96/05768 A1 2/1996

*Primary Examiner* — Eun Hwa Kim
*Assistant Examiner* — Rachel A. Vierra
(74) *Attorney, Agent, or Firm* — Dergosits & Noah LLP; Todd A. Noah

(57) ABSTRACT

A spine that may be used in the electrode assembly of an electrophysiologic catheter having controlled flexibility. The spine may have a flexible core that extends through a length of the spine, a polymeric cover and a plurality of electrodes, each having at least one lead, distributed longitudinally along the spine. An amount of material forming the spine may be adjusted longitudinally along the spine to compensate for changes in flexibility to the spine caused by varying numbers of electrode leads present at different relative longitudinal positions along the spine.

15 Claims, 5 Drawing Sheets

(56) References Cited

U.S. PATENT DOCUMENTS

| | | | |
|---|---|---|---|
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,748,255 B2 | 6/2004 | Fuimaono et al. | |
| 6,961,602 B2 | 11/2005 | Fuimaono et al. | |
| 6,973,340 B2 | 12/2005 | Fuimaono et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0176699 A1* | 9/2004 | Walker | A61B 5/015 600/549 |
| 2005/0215942 A1* | 9/2005 | Abrahamson | A61B 17/2202 604/22 |
| 2009/0171274 A1* | 7/2009 | Harlev | A61B 5/0422 604/95.04 |
| 2011/0213231 A1* | 9/2011 | Hall | A61B 5/0422 600/373 |
| 2012/0271135 A1* | 10/2012 | Burke | A61B 5/0422 600/373 |
| 2013/0172715 A1* | 7/2013 | Just | A61B 18/1492 600/374 |
| 2014/0194716 A1* | 7/2014 | Diep | A61B 5/6859 600/374 |
| 2014/0275921 A1* | 9/2014 | Harlev | A61B 5/0422 600/374 |
| 2015/0342532 A1* | 12/2015 | Basu | A61B 5/6858 600/374 |
| 2017/0007158 A1* | 1/2017 | Gross | A61B 5/063 |
| 2017/0112405 A1* | 4/2017 | Sterrett | A61B 5/6858 |
| 2017/0189106 A1* | 7/2017 | Schuler | A61B 18/02 |

\* cited by examiner

ELECTRODE ASSEMBLY HAVING SPINES WITH CONTROLLED FLEXIBILITY

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference. Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are positioned generally along the axis of the catheter body. Other electrode assembly configurations may be employed that also feature one or more spines having multiple electrodes. For example, commonly assigned U.S. Pat. No. 6,961,602, which is hereby incorporated by reference, discloses a multiray electrode assembly having two or more spines, attached at their proximal ends, but having free distal ends to allow the spines to assume desired shapes or conformations to more readily contact or otherwise be positioned adjacent the patient's tissue forming the anatomy being investigated or treated.

It is desirable that an electrode assembly be capable of detecting in as few beats as possible, including a single beat, as much of the electrical function of the region in which the electrode assembly is deployed, such as the left or right atrium. Accordingly, a goal in designing suitable electrode assemblies, whether employing basket-shaped or other configurations, is that the assembly reliably assume an intended deployed shape to efficiently and accurately record electrical signals from as many electrodes as possible. It will also be appreciated that a more complete picture of electrical activity in the heart may be obtained by increasing the density electrodes in the array. However, since each electrode requires its own leads, the cabling necessary for a relatively high number of electrodes may have a significant impact on the flexibility of the spines, resulting in the electrode assembly assuming a suboptimal deployed conformation. This effect is exacerbated by the need to include wiring for other components that may be included in an electrode assembly, including temperature sensors, position sensors and the like. Accordingly, the techniques of this disclosure as described in the following materials help compensate for variations in spine stiffness of an electrode assembly to control the flexibility of the spine.

SUMMARY

The present disclosure is directed to a spine for use in an electrode assembly of an electrophysiologic catheter. The spine may include a flexible core that extends through a length of the spine, a polymeric cover coaxially disposed over the flexible core and a plurality of electrodes distributed longitudinally along the spine over the polymeric cover, wherein each electrode has at least one associated lead that extends to a proximal end of the spine. An amount of material comprising the spine may be adjusted longitudinally along the spine to compensate for changes in flexibility to the spine caused by varying numbers of electrode leads present at different relative longitudinal positions along the spine.

In one aspect, the adjusted amount of material may be configured to provide the spine with more uniform flexibility along the length.

In one aspect, the spine may have relatively more material in a distal position as compared to a proximal position along the length of the spine.

In one aspect, the spine may have a filler material coaxially disposed between the polymeric cover and the flexible core to allow for adjusting the amount of material. For example, the adjusted amount of material may be a variable number of layers of filler material depending on relative longitudinal position along the spine. There may be more layers of filler material in a distal position as compared to a proximal position along the length of the spine. In one embodiment, a distal position may have two layers of filler material, an intermediate position may have one layer of filler material and a proximal position may have no layers of filler material.

In one aspect, each layer of filler material may be a shrink fit polymer.

In one aspect, the adjusted amount of material may be a tapered structural component.

This disclosure is also directed to a catheter with an elongated catheter body having proximal and distal ends and at least one lumen therethrough and an electrode assembly at the distal end of the catheter body, the electrode assembly comprising at least one spine having a proximal end connected to the catheter body, wherein the spine has a flexible core that extends through a length of the spine, a polymeric cover coaxially disposed over the flexible core and a plurality of electrodes distributed longitudinally along the spine over the polymeric cover, wherein each electrode has at least one associated lead that extends to a proximal end of the spine and wherein an amount of material comprising the spine may be adjusted longitudinally along the spine to compensate for changes in flexibility to the spine caused by varying numbers of electrode leads present at different relative longitudinal positions along the spine.

In one aspect, the catheter may have a plurality of spines connected at their proximal and distal ends configured as a basket-shaped electrode assembly, wherein the basket-shaped electrode assembly has an expanded arrangement wherein the spines bow radially outwardly and a collapsed arrangement wherein the spines are arranged generally along a longitudinal axis of the catheter body. The plurality of spines may be a framework formed from a laser cut tube of material.

Further, the disclosure includes a method for controlling spine flexibility. The method may involve providing a spine having a flexible core that extends through a length of the spine, a polymeric cover coaxially disposed over the flexible core and a plurality of electrodes distributed longitudinally along the spine over the polymeric cover, wherein each electrode has at least one associated lead that extends to a proximal end of the spine and adjusting an amount of material comprising the spine longitudinally along the spine to compensate for changes in flexibility to the spine caused by varying numbers of electrode leads present at different relative longitudinal positions along the spine.

In one aspect, the amount of material may be adjusted to provide the spine with more uniform flexibility along the length.

In one aspect, adjusting the amount of material may include varying a number of layers of filler material depending on relative longitudinal position along the spine. Adjusting the amount of material may include providing more layers of filler material in a distal position as compared to a proximal position along the length of the spine.

This disclosure also includes a method for treatment. The method may involve providing a catheter having an elongated catheter body with proximal and distal ends and at least one lumen therethrough and an electrode assembly at the distal end of the catheter body, the electrode assembly comprising at least one spine having a proximal end connected to the catheter body, wherein the spine has a flexible core that extends through a length of the spine, a polymeric cover coaxially disposed over the flexible core and a plurality of electrodes distributed longitudinally along the spine over the polymeric cover, wherein each electrode has at least one associated lead that extends to a proximal end of the spine and wherein an amount of material comprising the spine is adjusted longitudinally along the spine to compensate for changes in flexibility to the spine caused by varying numbers of electrode leads present at different relative longitudinal positions along the spine, advancing the distal end of the catheter with the electrode assembly to a desired region within a patient with the at least one spine in a collapsed arrangement that is generally aligned along a longitudinal axis of the catheter body and causing the electrode assembly to assume an expanded arrangement in which the at least one spine assumes an expanded arrangement, wherein the expanded arrangement is based at least in part on a flexibility of the spine resulting from the adjusted amount of material. Electrical signals may be received from the at least one electrode in contact with tissue.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
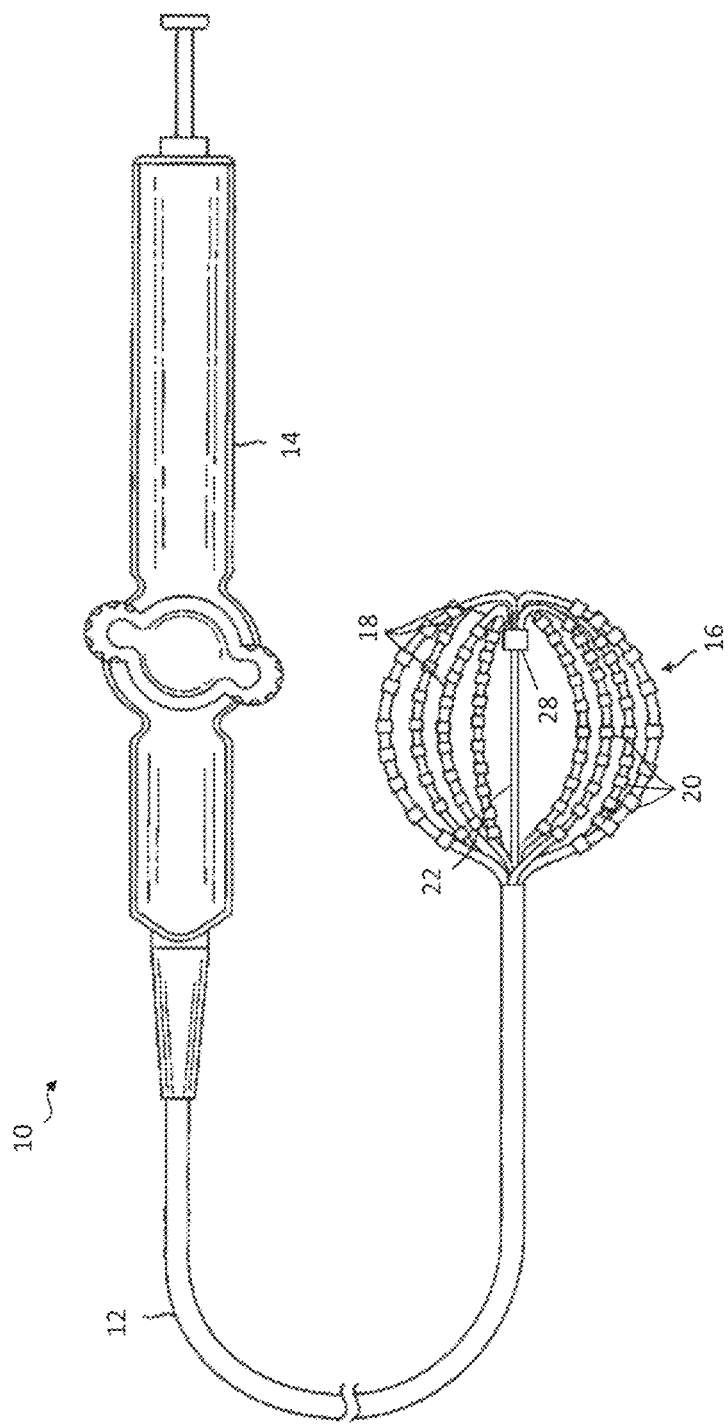
FIG. 1 is a top plan view of a catheter of the present invention, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. Thus, in one embodiment, all the points of the map or picture may be obtained simultaneously within one-tenth of a second. To facilitate such operations, an electrode assembly may be employed that conforms closely to the anatomy of the patient's heart in order to accurately map this electrical activity. Further, the resolution of the electrical activity map may be improved by employing an electrode array having increased density.

To help illustrate aspects of this disclosure, FIG. 1 schematically depicts an electrophysiologic catheter 10 that comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, it may be desirable to provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 20, such as at least ten and up to approximately 16 electrodes per spine. More electrodes are also possible. Similarly, the electrodes may be evenly distributed along the spine or may be skewed proximally, centrally or distally to facilitate analysis of the measured electrical signals.

When in a collapsed arrangement, the spines may be constrained, such as by a guiding sheath, and may be deflected from the collapsed arrangement to the expanded deployed arrangement by withdrawing the guiding sheath. As will be appreciated, in the collapsed arrangement, spines 18 assume a generally linear alignment with the catheter body 12 to minimize the outer diameter for insertion within and withdrawal from the patient. In the expanded arrangement, spines 18 of basket-shaped electrode assembly 16 bow outwards. When positioned at a desired location within a patient, assuming an expanded arrangement may bring electrodes 16 into contract or closer proximity with the walls of the chamber or other region in which basket-shaped electrode assembly 10 is positioned. The overall size of basket-shaped electrode assembly 10 may be selected based on the patient's anatomy to provide a close fit to the area of the patient being investigated or treated, such as the right or left atria.

In basket-shaped electrode assembly 16, the distal ends of spines 18 are secured together and optionally may be attached to a pulling member 22 that is generally coaxial with the catheter body 12 and extends from the proximal end of catheter body 12 through the central lumen. The pulling member is capable of longitudinal movement relative to the catheter body so that it can displace the distal ends of the spines 18 proximally relative to the catheter body 12 to radially expand the electrode assembly. Because the proximal ends of spines 18 may be secured at the catheter body 12, the distance between the distal and proximal ends of spines 14 may be shortened with relative movement of pulling member 22 in the proximal direction, causing spines 18 to bow outwards and assume an expanded arrangement. In some embodiments, spines 18 may have a preshaped expanded configuration that is assumed when unconstrained, such as through the use of a shape memory material as noted below, and do not require a pulling member.

Although aspects of this disclosure are described in the context of basket-shaped electrode assembly 16, the techniques may be applied to any electrode assembly that features spines adapted to provide an array of electrodes to occupy a three-dimensional space defined by the anatomy of the patient, such as a chamber of the heart or a vessel ostium for example. Accordingly, the expanded arrangement of the electrode assembly may have the generally spherical shape shown in FIG. 1, although configurations such as elliptical, ovoid, hemispherical or others may be employed as desired. Similarly, other electrode assemblies may also have one or more spines carrying the electrodes of the array that may have a preshaped expanded arrangement that facilitates deployment in a desired shape adapted to conform to the patient's anatomy, including the multiray electrode assemblies described above in which the distal ends of the spines are free. The expanded arrangement may help ensure sufficient contact between the electrodes and the target tissue. Regardless of whether a basket-shaped or other design is employed, the ability of the electrode assembly to assume its intended expanded arrangement and conform to the patient's anatomy is predicated on the flexibility of the spines. As used herein, the terms "flexibility" and "stiffness" may be used interchangeable to refer to the relative compliance of the spine.

In some embodiments, a shape memory material may be used to aid assuming the expanded and collapsed arrangements. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and super elasticity which allow nitinol to have a "memorized shape" that is dependent on its temperature phases. The austenite phase is nitinol's stronger, higher-temperature phase, with a simple cubic crystalline structure. Super elastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, an electrode assembly, such as basket-shaped electrode assembly 16, when formed from such materials may have a three-dimensional shape that may be collapsed to be fed into a guiding sheath and then readily returned to its expanded shape memory configuration upon delivery to the desired region of the patient upon removal of the guiding sheath and/or actuation of a pulling member. In one exemplary embodiment, a framework comprising some or all the spines 18 may be formed from a nitinol hypotube by laser cutting or other similar techniques, to provide a monolithic framework. Depending on the embodiment, a 3 mm tube having a wall thickness of approximately 8 to 9 mil may be used. Alternative embodiments may employ other materials do not necessarily have shape memory characteristics, but have sufficient resilience to assume the expanded and collapsed arrangements, including metallic materials such as stainless steel or polymeric materials such as polyetheretheketone (PEEK).

Figure 2:
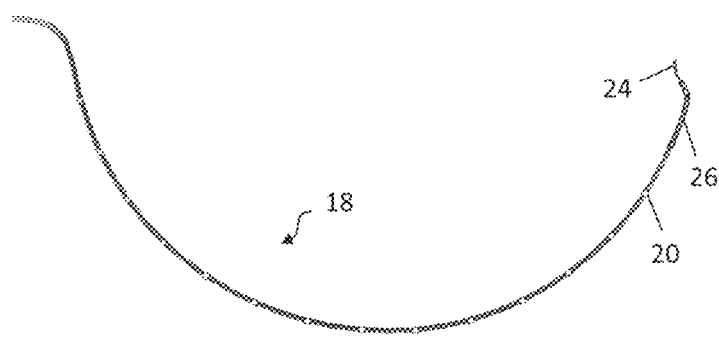
FIG. 2 is a schematic view of a spine having controlled flexibity, according to one embodiment.

In the embodiments of this disclosure, each spine (such as spine 18 of basket-shaped electrode assembly 16) comprises multiple electrodes, commonly several. Correspondingly, each electrode requires its own lead(s) to conduct the electrical signals received at the electrodes through the catheter for recording and processing by instrumentation coupled to the catheter. The spines may be formed using a core substrate, such as a shape memory wire, coaxially disposed within a polymeric tube. For example, a single spine 18 is shown in detail in FIG. 2 and may be constructed by employing the noted substrate material to form flexible core 24 that is coaxially disposed within a polymeric cover 26. Electrodes 20 may be configured as ring electrodes and may be secured over polymeric cover 26, such as by crimping, in conjunction with welding, soldering or otherwise forming an electrical connection with one or more leads. Correspondingly, each ring electrode 20 may be installed lengthwise along spine 18 and connected to at least one corresponding lead. Since each electrode 20 has at least one lead, a cross section taken along spine 18 will include all the leads corresponding to electrodes 20 that are at distal positions relative to the cross section. Similarly, any other components that may be carried by catheter body 12 that require wiring will also have leads at any proximal location. For example, one or more position sensors 28 (as shown in FIG. 1) may be at known locations relative to the distal end of catheter body 12 to help visualize the catheter within a patient. A variety of other components, including temperature sensors, contact sensors, ablation electrodes, and the like may be deployed by catheter 10. As a result, the number of leads at a given location is directly related to its relative longitudinal position, given that the electrodes and components are distributed along the length of spine 18.

The existence of a relatively more cabling at proximal locations along the spine as compared to distal locations may cause the flexibility of spine 18 to vary significantly along its length. Accordingly, the amount of the cross section filled at distal and proximal positions may differ enough to significantly affect the stiffness of spine 18. Correspondingly, the techniques of this disclosure are directed to controlling the flexibility of spines 18 along their longitudinal length. In one aspect, this may include creating a more uniform compliance profile to reduce the difference in stiffness between proximal and distal locations. In general, the amount of material provided at a given longitudinal position along spine 18 may be adjusted to help compensate for the amount of cabling for distal electrodes and components that may be present at that position. For example, to obtain more uniformity in the resulting stiffness of spine 18, there may be relatively more material at distal locations relative to proximal locations along its length. However, depending on the embodiment, it may be advantageous to utilize a spine that exhibits variable compliance characteristics along its length. For example, the flexibility may be adjusted to help provide force to hold one or more of electrodes 20 in contact with tissue, given the anticipated dimensions of the space in which the electrode assembly is deployed. As such, the amount of material used to form spine 18 at different relative longitudinal positions may be tailored to achieve a desired stiffness.

Figure 3:
FIG. 3 is a schematic view of a tapered flexible core for a spine, according to one embodiment.
Figure 4:
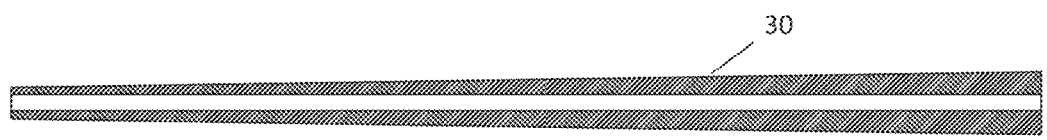
FIG. 4 is a schematic view of a tapered tubular member for a spine, according to one embodiment.

In one aspect, a suitable adjustment of the amount of material may be achieved by tapering one or more of the structural components forming spine 18, such as the substrate that may include flexible core 20 and/or any coverings, including polymeric tube 22. The degree, direction and location of taper may depend on the desired compliance profile. Again, in the context of achieving more uniform flexibility, the taper may be from a relatively greater dimension at distal locations to a relatively smaller dimension at proximal locations. Adjusting the amount of material along a longitudinal direction of spine 18 may include adding one or more layers of material, each of which may be tapered as desired. As illustrations only and without limitation, FIG. 3 schematically depicts a portion of a tapering flexible core 24 in a longitudinal cross section and FIG. 4 schematically depicts a portion of a tapering tubular member 30, also in cross section, which may be used in place of polymeric cover 26 or may be an additional structural component that is coaxially disposed over spine 18, such as between flexible core 24 and polymeric cover 26. In some embodiments, the outer component of spine 18, such as polymeric cover 26, may be configured to exhibit a relatively constant outer diameter to allow electrodes 20 to be uniform, facilitating attachment and helping to ensure consistent measurement of electrical signals.

Figure 5:
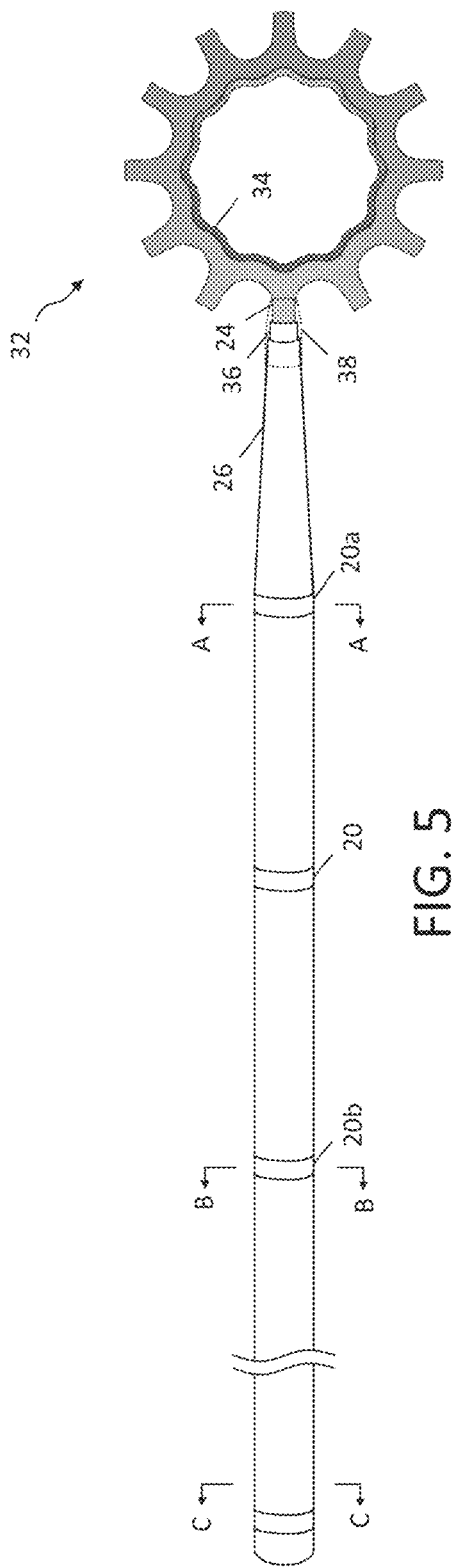
FIG. 5 is an end view that schematically depicts a framework for a basket-shaped electrode assembly and a spine having controlled flexibility, according to one embodiment.

Given that tapering a component may represent a more involved manufacturing process, it may be desirable to adjust the amount of material along a longitudinal direction of spine 18 by adding one or more layers of a suitable material. Although each layer may have a relatively constant thickness, the amount of material may be adjusted by including or omitting a layer depending on the longitudinal position. Each layer may have the same or different thickness. Accordingly, the amount of material may also be adjusted by stacking multiple layers, again depending on the longitudinal position along spine 18. As one example, FIG. 5 schematically depicts an end view of a framework 32 used to create basket-shaped electrode assembly 16, which as noted above, may be laser cut from a tube of suitable material such as a shape memory alloy. Distal hub 34 may be formed by an intact portion of the tube, so that the distal ends of spines 18 are secured together. For clarity, only one extended portion of the twelve spines 18 of this embodiment is shown, with polymeric cover 26 coaxially disposed over flexible core 24. Further, these figures are not drawn to scale, but are rather intended simply to show the relationship between the various components. As discussed above, one or more layers of filler material 36 may be provided at various locations along the length of spine 18 to achieve the desired control of spine flexibility. As an example, the layers of filler material 36 may be formed from shrink fit tubing, although other suitable materials may also be employed. In this embodiment, the distal end of polymeric tube 22 may be sealed and further secured to framework 42 with a short length of shrink fit material 38, shown here in phantom.

Figure 8:
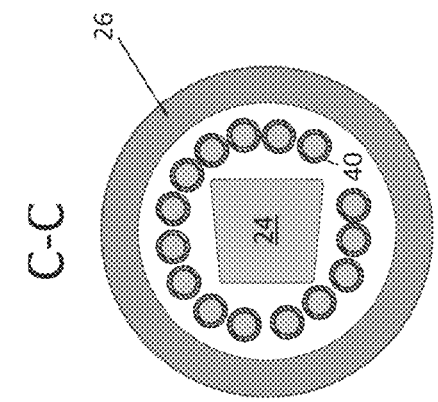
FIG. 8 is a cross sectional view of the spine shown in FIG. 5 at a proximal position, according to one embodiment.
Figure 7:
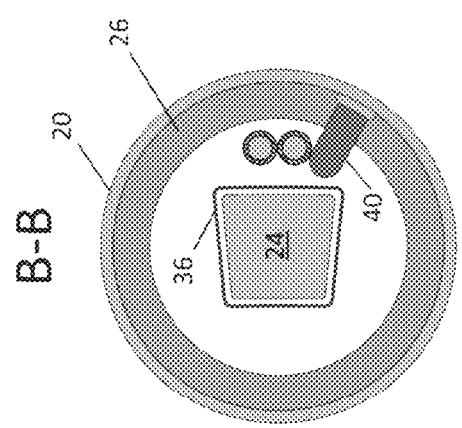
FIG. 7 is a cross sectional view of the spine shown in FIG. 5 at an intermediate position, according to one embodiment.
Figure 6:
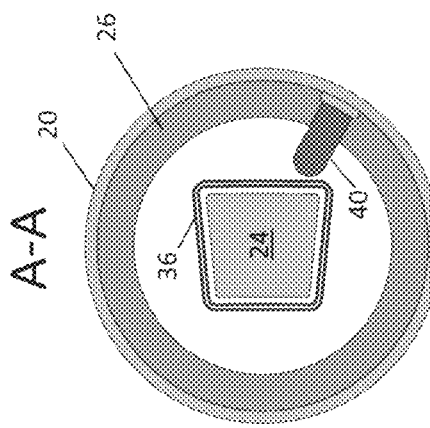
FIG. 6 is a cross sectional view of the spine shown in FIG. 5 at a distal position, according to one embodiment.

According to the techniques of this disclosure, the amount of material provided along the length of spine may be adjusted by selectively adding layers of filler material 36 depending on the longitudinal position. For example, FIG. 6 shows a cross section of spine 18 along the line A-A, taken at the distal most electrode location. Correspondingly, a single lead 40 is shown, which is associated with distal most electrode 20a. In this embodiment, two layers of filler material 36 are disposed over flexible core 24 at this location. For comparison, FIG. 7 shows a cross section of spine 18 taken along the line B-B, the location of the third most distal electrode 20b. As shown, lead 40 is connected to this electrode, while two additional leads are present that couple to the two more distal electrodes. In this embodiment, one layer of filler material 36 is disposed over flexible core 24 at this location. Further, FIG. 8 shows a cross section of spine 18 taken along the line C-C at a location proximal to the fifteenth electrode, so that fifteen leads 40 are present. In this embodiment, the filler material is omitted along this portion of flexible core 24. It will be appreciated that the configuration described in reference to FIGS. 5-8 is one embodiment only and that any desired number of layers of filler material, including no layers, may be used at varying longitudinal positions to achieve desired flexibility characteristics in the resulting spine. Further, although this embodiment is generally directed to providing a more uniform flexibility along the length of spine 18, in other embodiments the amount of material may be adjusted in a manner that provides a varying compliance profile if desired.

Exerting greater control over the stiffness of the spines of an electrode assembly according to the techniques of this disclosure may allow the assembly to more readily assume the intended expanded arrangement. In one aspect, this may include conforming more closely to the patient's anatomy. These techniques may also improve the safety profile of the electrode assembly by reducing the chance of the spine collapsing or otherwise kinking due to unwanted variations in spine flexibility.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 9:
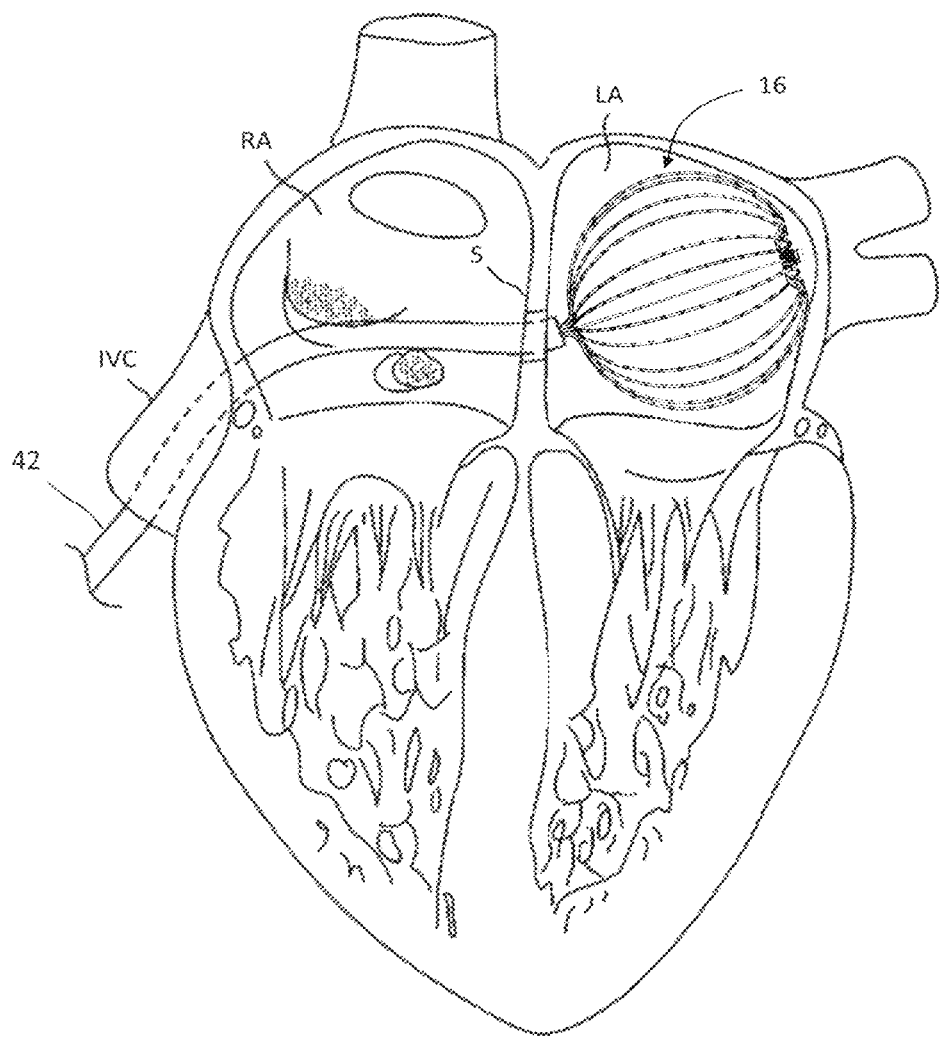
FIG. 9 is a schematic view of a basket-shaped electrode assembly having spines with controlled flexibility deployed within the left atrium, according to one embodiment.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the puller permits the catheter to pass over the guidewire. In one exemplary procedure as depicted in FIG. 9, the catheter is first introduced to the right atrium (RA) via the inferior vena cava (IVC), where it passes through the septum (S) in order to reach the left atrium (LA).

As will be appreciated, guiding sheath 42 covers the spines 18 of the basket-shaped electrode assembly 16 in a collapsed arrangement so that the entire catheter can be passed through the patient's vasculature to the desired location. A puller member, if provided, may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the basket-shaped electrode assembly 16. The puller member, if present, may be drawn proximally through a range of travel or otherwise manipulated so that the spines 18 flex outwardly between the distal and proximal junctions. Alternatively or in addition, basket-shaped electrode assembly 16 may assume the expanded arrangement upon withdrawal of guiding sheath 42 due to the preshaped characteristics of spines 18. With either configuration, basket-shaped electrode assembly 16 may assume its intended expanded arrangement more reliably due to the control over spine flexibility imparted by the techniques described above. With the basket-shaped electrode assembly 16 radially expanded, the ring electrodes 20 contact atrial tissue. When the basket-shaped electrode assembly 16 is in its expanded arrangement, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the inventive catheter with the multiple electrodes on the basket-shaped electrode assembly, the electrophysiologist can obtain a true anatomy of a cavernous region of the heart, including an atrium, by measuring less points than with traditional catheters, allowing a more rapid mapping of the region.

Figure 10:
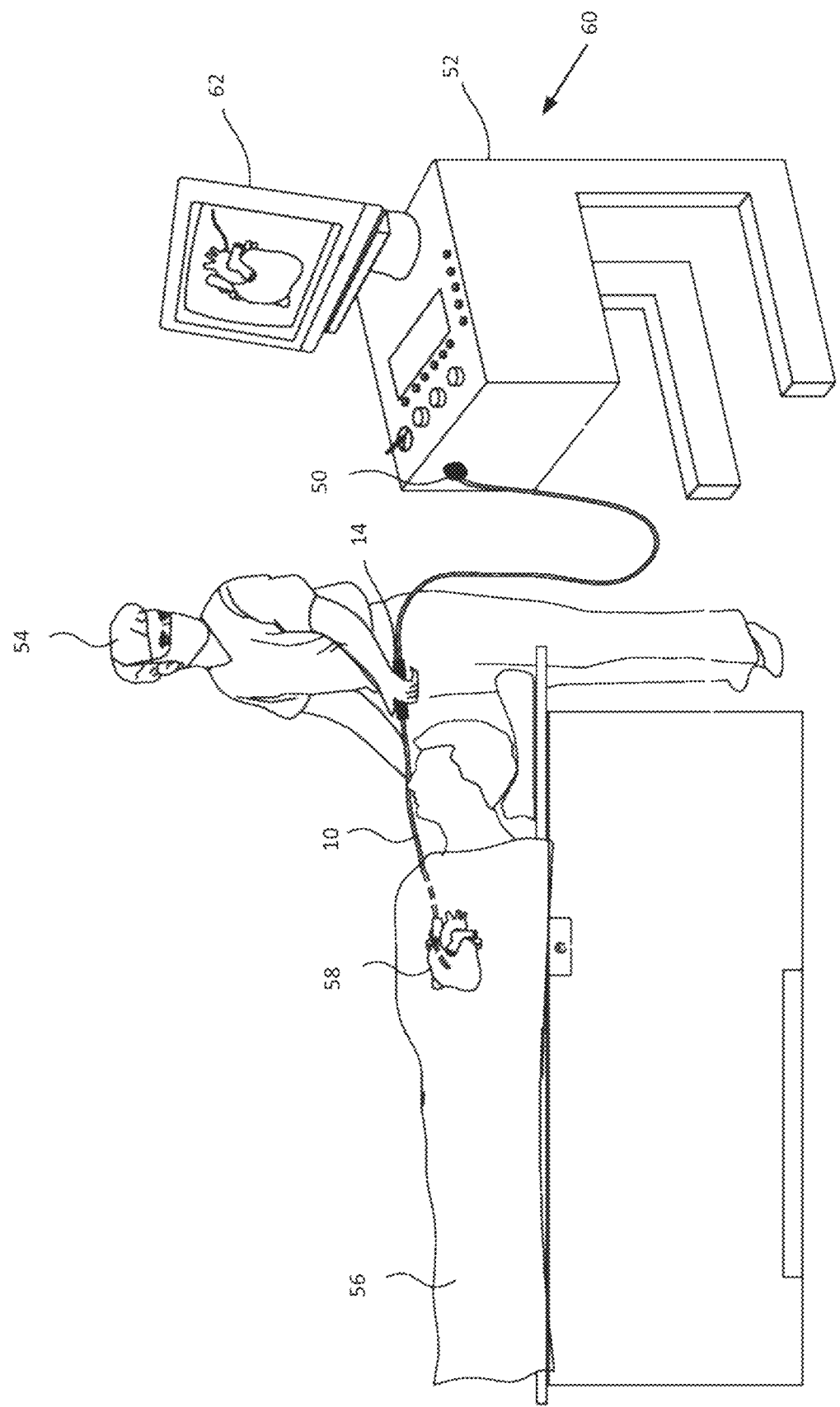
FIG. 10 is a schematic illustration of an invasive medical procedure using an electrode assembly having a spine with controlled flexibility, according to one embodiment.

To help illustrate use of the basket-shaped electrode assembly 16, FIG. 10 is a schematic depiction of an invasive medical procedure, according to an embodiment of the present invention. Catheter 10, with the basket-shaped electrode assembly 16 having spines with controlled flexibility (not shown in this view) at the distal end may have a connector 50 at the proximal end for coupling the wires from their respective electrodes 20 (not shown in this view) to a console 52 for recording and analyzing the signals they detect. An electrophysiologist 54 may insert the catheter 10 into a patient 56 in order to acquire electropotential signals from the heart 58 of the patient. The professional uses the control handle 14 attached to the catheter in order to perform the insertion. Console 52 may include a processing unit 60 which analyzes the received signals, and which may present results of the analysis on a display 62 attached to the console. The results are typically in the form of a map, numerical displays, and/or graphs derived from the signals.

In a further aspect, the processing unit 60 may also receive signals from one or more location sensors 28 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 60 to determine the position, (e.g., the location and orientation) of the distal end of catheter 10 within the heart cavity. The electrophysiologist may then view the position of the basket-shaped electrode assembly 16 on an image the patient's heart on the display 62. By way of example, this method of position sensing may be implemented using the CARTO™ system, produced by Biosense Webster Inc. (Diamond Bar, Calif.) and is described in detail in U.S. Pat. Nos. 5,391,199, 5,690,963, 5,484,118, 5,239,724, 5,618,612 and 5,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 20.

The preceding description has been presented with reference to presently disclosed embodiments of the invention.

Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A spine for use in an electrode assembly of an electrophysiologic catheter comprising: a flexible core that extends through a length of the spine; a polymeric cover coaxially disposed over the flexible core; a filler material coaxially disposed between the polymeric cover and the flexible core; and a plurality of electrodes distributed longitudinally along the spine over the polymeric cover; wherein each electrode has at least one associated lead that extends to a proximal end of the spine, the at least one lead disposed between the filler material and the polymeric cover; the flexible core, the polymeric cover and the filler material forming the spine, wherein the filler material comprises at least one layer of filler material; and wherein an amount of the at least one layer of filler material forming the spine is adjusted longitudinally along the spine based on changes in flexibility to the spine caused by varying numbers of electrode leads present at different relative longitudinal positions along the spine, the at least one layer of filler material having a variable number of layers of filler material depending on the different relative longitudinal positions along the spine and the number of electrode leads present at the different relative longitudinal positions.

2. The spine of claim 1, wherein the adjusted amount of the at least one layer of filler material is configured to provide the spine with more uniform flexibility along the length.

3. The spine of claim 1, wherein there are more layers of the at least one layer of filler material in a distal position as compared to a proximal position along the length of the spine.

4. The spine of claim 1, wherein there are more layers of the at least one layer of filler material in a distal position as compared to a proximal position along the length of the spine.

5. The spine of claim 4, wherein a distal position comprises two layers of the at least one layer of filler material, an intermediate position comprises one layer of the at least one layer of filler material and a proximal position comprises no layers of the at least one layer of filler material.

6. The spine of claim 1, wherein each layer of the at least one layer of filler material comprises a shrink fit polymer.

7. The spine of claim 1, wherein the adjusted amount of the at least one layer of filler material comprises a tapered structural component.

8. A catheter comprising an elongated catheter body having proximal and distal ends and at least one lumen therethrough and an electrode assembly at the distal end of the catheter body, the electrode assembly comprising at least one spine having a proximal end connected to the catheter body, wherein the spine has a flexible core that extends through a length of the spine, a polymeric cover coaxially disposed over the flexible core, a filler material coaxially disposed between the polymeric cover and the flexible core, and a plurality of electrodes distributed longitudinally along the spine over the polymeric cover, wherein each electrode has at least one associated lead that extends to a proximal end of the spine, the at least one lead disposed between the filler material and the polymeric cover; the flexible core, the polymeric cover and the filler material forming the spine, wherein the filler material comprises at least one layer of filler material, and wherein an amount of the at least one layer of filler material forming the spine is adjusted longitudinally along the spine based on changes in flexibility to the spine caused by varying numbers of electrode leads present at different relative longitudinal positions along the spine, the at least one layer of filler material having a variable number of layers of filler material depending on the different relative longitudinal positions along the spine and the number of electrode leads present at the different relative longitudinal positions.

9. The catheter of claim 8, further comprising a plurality of spines connected at their proximal and distal ends configured as a basket-shaped electrode assembly, wherein the basket-shaped electrode assembly has an expanded arrangement wherein the spines bow radially outwardly and a collapsed arrangement wherein the spines are arranged generally along a longitudinal axis of the catheter body.

10. The catheter of claim 9, wherein the plurality of spines comprise a framework formed from a laser cut tube of material.

11. A method for controlling spine flexibility comprising:
providing a spine having a flexible core that extends through a length of the spine, a polymeric cover coaxially disposed over the flexible core, a filler material coaxially disposed between the polymeric cover and the flexible core, and a plurality of electrodes distributed longitudinally along the spine over the polymeric cover, wherein each electrode has at least one associated lead that extends to a proximal end of the spine, the at least one lead disposed between the filler material and the polymeric cover; the flexible core, the polymeric cover and the filler material forming the spine, wherein the filler material comprises at least one layer of filler material; and
adjusting an amount of the at least one layer of filler material forming the spine longitudinally along the spine based on changes in flexibility to the spine caused by varying numbers of electrode leads present at different relative longitudinal positions along the spine, the at least one layer of filler material having a variable number of layers depending on a relative longitudinal position along the spine and the number of electrode leads present at that relative longitudinal position.

12. The method of claim 11, wherein adjusting the amount of the at least one layer of filler material provides the spine with more uniform flexibility along the length.

13. The spine of claim 11, wherein adjusting the amount of the at least one layer of filler material comprises providing more layers of the at least one layer of filler material in a distal position as compared to a proximal position along the length of the spine.

14. A method for treatment comprising:
providing a catheter having an elongated catheter body with proximal and distal ends and at least one lumen therethrough and an electrode assembly at the distal end of the catheter body, the electrode assembly comprising at least one spine having a proximal end connected to the catheter body, wherein the spine has a flexible core that extends through a length of the spine, a polymeric cover coaxially disposed over the flexible core, a filler material coaxially disposed between the polymeric cover and the flexible core, and a plurality of electrodes distributed longitudinally along the spine over the polymeric cover, wherein each electrode has at least one associated lead that extends to a proximal end of the spine, the at least one lead disposed between the filler material and the polymeric cover; the flexible core, the polymeric cover and the filler material forming the spine, wherein the filler material comprises at least one layer of filler material, and wherein an amount of the at least one layer of filler material forming the spine is adjusted longitudinally along the spine based on changes in flexibility to the spine caused by varying numbers of electrode leads present at different relative longitudinal positions along the spine, the at least one layer of filler material having a variable number of layers of filler material the different relative longitudinal positions along the spine and the number of electrode leads present at the different relative longitudinal positions;

advancing the distal end of the catheter body with the electrode assembly to a desired region within a patient with the at least one spine in a collapsed arrangement that is generally aligned along a longitudinal axis of the catheter body; and causing the electrode assembly to assume an expanded arrangement in which the at least one spine assumes an expanded arrangement, wherein the expanded arrangement is based at least in part on a flexibility of the spine resulting from the adjusted amount of the at least one layer of filler material.

15. The method of claim 14, further comprising receiving electrical signals from the plurality of electrodes in contact with tissue.

\* \* \* \* \*